United States Patent
Magaraggia et al.

(10) Patent No.: US 11,250,565 B2
(45) Date of Patent: Feb. 15, 2022

(54) MEDICAL ASSISTANCE DEVICE, SYSTEM, AND METHOD FOR DETERMINING A DEFORMATION OF A SUBJECT, COMPUTER PROGRAM, CORRESPONDING COMPUTER-READABLE STORAGE MEDIUM

(71) Applicant: Siemens Healthcare GmbH, Erlangen (DE)

(72) Inventors: Jessica Magaraggia, Erlangen (DE); Gerhard Kleinszig, Forchheim (DE); Maddalena Strumia, Forchheim (DE); Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 109 days.

(21) Appl. No.: 16/728,242

(22) Filed: Dec. 27, 2019

(65) Prior Publication Data
US 2020/0219253 A1    Jul. 9, 2020

(30) Foreign Application Priority Data
Jan. 3, 2019 (EP) .................................... 19150246

(51) Int. Cl.
*G06K 9/00* (2006.01)
*A61B 6/00* (2006.01)
(Continued)

(52) U.S. Cl.
CPC ............ *G06T 7/0012* (2013.01); *A61B 34/20* (2016.02); *A61B 34/37* (2016.02); *G06T 7/149* (2017.01);
(Continued)

(58) Field of Classification Search
USPC ................ 382/100, 103, 106–107, 128–132, 382/153–154, 168, 173, 181, 199, 214,
(Continued)

(56) References Cited

U.S. PATENT DOCUMENTS 9,375,184 B2    6/2016  Boettger
10,130,345 B2   11/2018 Wong
(Continued)

FOREIGN PATENT DOCUMENTS

WO    WO2012114224 A1    8/2012
WO    WO2015044838 A1    4/2015

OTHER PUBLICATIONS

European Search Report for European Patent Application No. 19150246.7—1122 dated Jul. 16, 2019.
Fischer, Peter, et al. "Surrogate-driven estimation of respiratory motion and layers in x-ray fluoroscopy." International Conference on Medical Image Computing and Computer-Assisted Intervention. Springer, Cham, 2015.

*Primary Examiner* — Seyed H Azarian
(74) *Attorney, Agent, or Firm* — Lempia Summerfield Katz LLC

(57) ABSTRACT

A medical assistance device, a system, and a method are provided for determining a deformation of a subject. Undisturbed image data of the subject and pose data of a robotic instrument are acquired. The medical assistance device is configured to determine the deformation of the subject due to a physical contact between the subject and the robotic instrument based on a biomechanical model. The undisturbed image data and a pose and/or motion of the robotic instrument are provided as input to the biomechanical model. The biomechanical model is predetermined or generated and/or updated based on a strain and/or a stiffness measured by a sensor.

15 Claims, 1 Drawing Sheet

(51) Int. Cl.
  *G06T 7/00*      (2017.01)
  *A61B 34/20*     (2016.01)
  *A61B 34/37*     (2016.01)
  *G06T 7/215*     (2017.01)
  *G06T 7/149*     (2017.01)
  *G06T 7/246*     (2017.01)

(52) U.S. Cl.
  CPC .............. *G06T 7/215* (2017.01); *G06T 7/251* (2017.01); *A61B 2034/2059* (2016.02); *G06T 2207/10072* (2013.01); *G06T 2207/10121* (2013.01); *G06T 2207/10136* (2013.01); *G06T 2207/30004* (2013.01)

(58) Field of Classification Search
  USPC ........ 382/224, 254, 286–291, 305, 321; 1/1; 600/407, 431, 466; 378/4, 21
  See application file for complete search history.

(56) References Cited

U.S. PATENT DOCUMENTS

| | | | | |
|---|---|---|---|---|
| 2006/0253032 | A1* | 11/2006 | Altmann | A61B 6/488 |
| | | | | 600/466 |
| 2007/0197896 | A1* | 8/2007 | Moll | A61B 1/00039 |
| | | | | 600/407 |
| 2013/0063434 | A1 | 3/2013 | Miga | |
| 2014/0343416 | A1* | 11/2014 | Panescu | A61B 34/10 |
| | | | | 600/431 |
| 2019/0350660 | A1* | 11/2019 | Moll | A61B 8/12 |
| 2021/0030494 | A1* | 2/2021 | Panescu | A61N 5/1077 |

\* cited by examiner

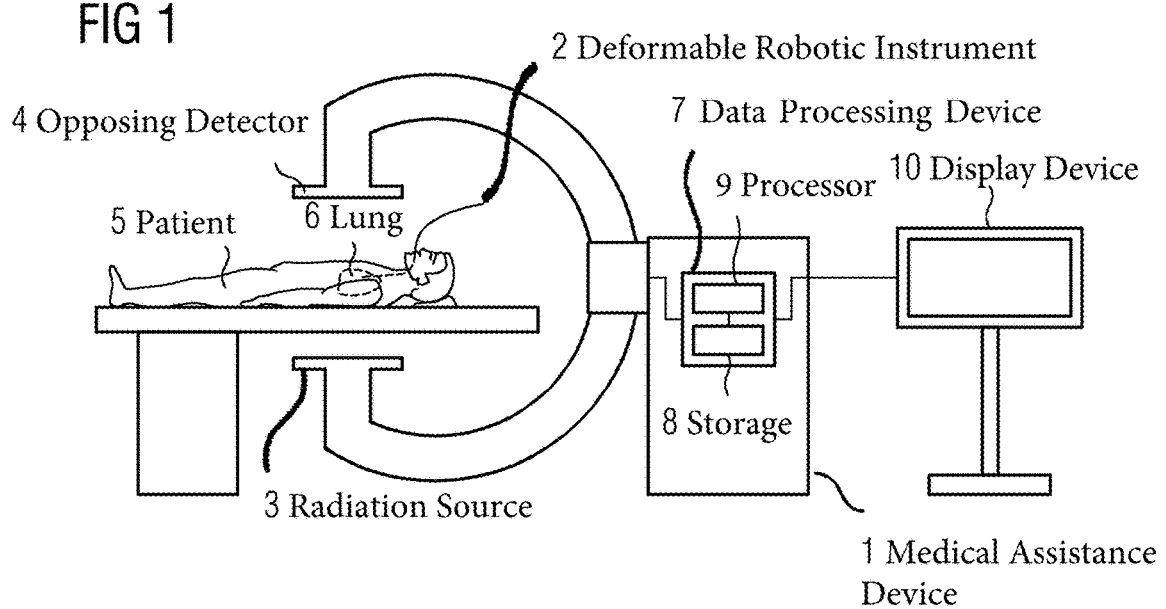
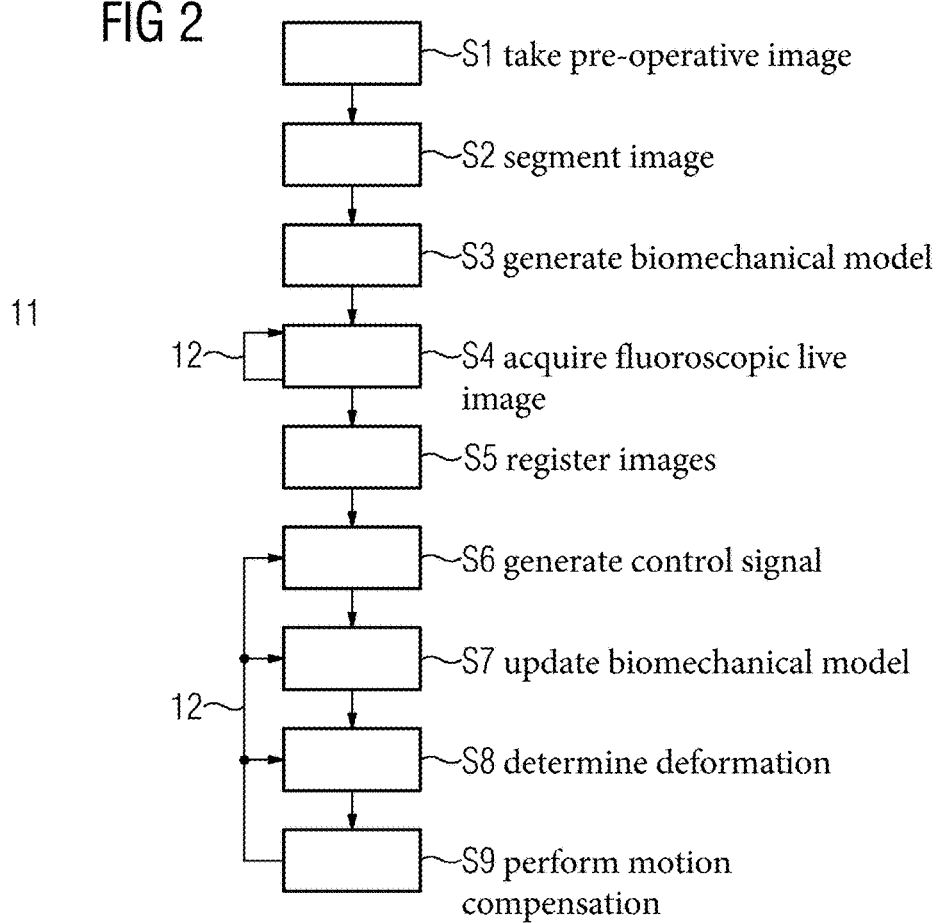

MEDICAL ASSISTANCE DEVICE, SYSTEM, AND METHOD FOR DETERMINING A DEFORMATION OF A SUBJECT, COMPUTER PROGRAM, CORRESPONDING COMPUTER-READABLE STORAGE MEDIUM

CROSS REFERENCE TO RELATED APPLICATIONS

This application claims the benefit of EP 19150246.7, filed on Jan. 3, 2019 which is hereby incorporated by reference in its entirety.

FIELD

Embodiments relate to a medical assistance device, a system, and a method for determining a deformation of a subject.

BACKGROUND

With intra-body procedures or interventions, a need for a surgeon or physician to be able to reach and clearly see a region of interest is often at odds with the desire to minimize a trauma for a respective subject or patient. With procedures such as minimally invasive surgery, bronchoscopy, endovascular or gastro-intestinal endoscopy, and others the trauma for the patient may be minimized when compared to fully invasive open surgery. The techniques do, however, face the problem that a respective instrument or medical tool has to be navigated to a region of interest that may not be directly observable by the surgeon. Past approaches to the problem include acquiring a pre-operative or pre-operational dataset of the respective patient as a basis for planning a path of the respective instrument or medical tool, and/or monitoring a progress of the instrument or medical tool during the procedure with live imaging techniques, such as fluoroscopic guidance.

The approaches still face multiple problems. For example, there may be anatomical deformation and shifting or displacement of parts of the anatomy, for example due to a respiratory motion, a heartbeat, and/or due to contact between the patient and the instrument or medical tool itself. Contact may be when the patient's anatomy and the instrument or tool physically interact with each other. As a consequence, the intra-body path for the instrument, for example to reach a lung lesion to perform a biopsy, based on pre-operative data may be highly inaccurate and may lead to several unsuccessful attempts to reach the respective region of interest and/or to a failure of the entire procedure. This is the case, because at any time, when the procedure or intervention is performed, an insertion of the instrument and guiding the instrument through the patient, in addition to the deformation due to the breathing motion and/or heartbeat causes a tissue deformation or displacement that is not accounted for in the pre-operative dataset, for example, a pre-op CT-image. Therefore, the planned or pre-computed path for the instrument may not reflect the intra-procedural patient anatomy. Specifically, the position of the respective region of interest, for example a position or location of a lesion, may change.

A navigation of an instrument through the airways is challenging since no contrast agent may be used during the respective procedure or intervention that makes the airways essentially invisible under fluoroscopic imaging. Since there is no live reference, such as a highly contrasted vessel tree, available during navigation through the airways, traditional approaches, such as providing an overlay of a structure of the anatomy or the region of interest may be challenging to achieve with correct relative positioning. An obsolete or inaccurate overlay or positioning of the overlay may also lead to multiple tentative navigation attempts during the insertion or navigation of, for example, a bronchoscope, and overall does not support a surgeon or physician or medical personnel in effectively and efficiently reaching or navigating to a region of interest, such as a peripheral lesion.

One approach is detailed in the publication "Surrogate-Driven Estimation of Respiratory Motion and Layers in X-Ray Fluoroscopy" by Peter Fisher at al., published under DOI: 10.1007/978-3-319-24553-9_35. To attain plausible motions, prior information for each motion layer is included in the form of a surrogate signal. A respiratory signal is extracted from images using manifold learning. The respiratory signal is then used to define a surrogate-driven motion model that is incorporated into an energy minimization framework with smoothness priors to enable motion estimation. The approach does, however, require the estimation of a motion model from a breathing cycle and does not account for any deformations or anatomical shifts due to an inserted instrument or tool, and relies on a regularity of the breathing that cannot reliably be ensured in most patients.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide technical assistance to medical personnel during a procedure involving a robotic instrument.

A medical assistance device includes at least a data acquisition unit and a data processing unit. The medical assistance device may, for example, be or include a computer. The data acquisition unit may include an interface over which data may be acquired from one or more different external sources such as a medical imaging device or data store. The medical assistance device may include an imaging device or imaging modality, such as for example an x-ray device or MRI device (MRI: magnetic resonance imaging), or ultrasound device or the like, that is configured to image a subject, such as a patient or a part of a patient. Acquiring corresponding image data may include measuring or capturing such image data directly from a respective subject.

The data acquisition unit is configured to acquire undisturbed image data of a subject and pose data of a robotic instrument relative to a coordinate system of the undisturbed image, that is, a coordinate system of an imaging device or imaging modality used to capture the undisturbed image data. The undisturbed image data shows the subject while not being deformed, displaced, or influenced by the robotic instrument. Undisturbed has the meaning of not being deformed, displaced or influenced by the robotic instrument. The undisturbed image data of the subject may, for example, be or include a pre-operative image or image dataset, such as a CT- or MR-image, for example, a 3D-image. The undisturbed image data may be or include a segmentation of the subject or an image or image dataset of the subject.

The pose data of the robotic instrument may, for example, include or define or characterize a pose and/or a motion of the robotic instrument, as well as its geometry or shape and/or changes thereof. For example, the pose data may be spatially resolved and/or time-resolved, meaning that the robotic instrument may be tracked to acquire or define the pose data. Tracking the robotic instrument and/or acquiring or determining the pose data may be achieved through different methods, for example by a tracking system, such as an electromagnetic tracking system, that may track the robotic instrument itself and/or one or more positional markers arranged on or as part of the robotic instrument. Other possibilities are described below. The robotic instrument may, for example, be or include a robotically controllable catheter or endoscope, for example in the form of a "snake robot", a probe, a biopsy instrument, and/or the like.

The data processing unit is connected to the data acquisition unit and configured to determine a deformation of the subject due to a physical or mechanical contact between the robotic instrument and the subject. The data processing unit is configured to determine the deformation based on a biomechanical model of the subject, the undisturbed image data, and a pose and/or motion of the robotic instrument specified by the pose data. The pose data, for example the pose and/or motion of the robotic instrument, is provided as input to the biomechanical model. The undisturbed image data may also be provided to the biomechanical model as further input, for example, to serve as a spatial reference point to determine or define the deformation, that is, any movement, displacement, and/or change in form or shape of the subject, or a part thereof due to the robotic instrument.

The biomechanical model may be predetermined, meaning that the biomechanical model may be pre-assembled or pre-defined and stored on a data store, a storage device, or a storage medium of the medical assistance device, for example of the data processing unit. The biomechanical model may be predetermined based on or generated from the undisturbed image data. Alternatively, the biomechanical model may be, for example automatically generated and/or updated based on a strain and/or a stiffness measured by a sensor system of the robotic instrument and acquired by the data acquisition unit. The strain and/or stiffness may be the strain and/or stiffness of the subject and/or of the robotic instrument.

The sensor system of the robotic instrument may include one or multiple strains sensors, stiffness sensors, pressure sensors, force sensors, momentum sensors, angulation sensors, and/or the like. Sensor data measured and provided by the sensor system may be automatically acquired by the data acquisition unit over a corresponding data link or data connection between the data acquisition unit or the medical assistance device and the robotic instrument. The data link or data connection may be wired or wireless.

The biomechanical model may be generated from a pre-operative dataset of the individual subject, such as the undisturbed image data. Alternatively, a generic biomechanical model may be used, for example a biomechanical model of a specific section of the human body or of a type of organ.

The biomechanical model being predetermined may provide for a realization and application of the present invention with reduced on-site resources, that is, with a medical assistance device including relatively low computational power. Generating and/or updating the biomechanical model during use or operation of the medical assistance device may provide for improved flexibility, accuracy, and/or customizability. For example, depending on an equipment or configuration of the robotic instrument, situational requirements, and/or depending on at which part of the respective subject the robotic instrument is used, different parameters or properties might be determined to define, customize, or adapt the biomechanical model. It is also possible to combine the possibilities, meaning that the biomechanical model may be predetermined and then be updated, or adapted. Updating the biomechanical model may, for example, include changing a predetermined, assumed, or estimated value for one or more properties, such as a stiffness of the subject, or a part of the subject, a size of the subject, a distance between the subject and a neighboring tissue, and/or the like to a value that has been measured or determined based on the pose data and/or the sensor data acquired from the robotic instrument. For example, the robotic instrument may be in contact with the subject along at least a stretch of its length, that might be determined from a measured pressure and/or resistance to movement of the robotic instrument. Based on the pressure or a corresponding force and/or a curvature of the robotic instrument, the size, curvature, and/or a stiffness of the subject may be determined.

The biomechanical model may model or simulate or characterize a mechanical behavior of the subject, its elasticity, its fluid dynamic properties, its compressibility, limits to its possible motions and/or to its deformation due to its internal structure, due to surrounding tissues, and/or due to connections to surrounding tissues, and/or the like. A biomechanical model may be prepared in advance with arbitrary accuracy. Adapting or tuning the biomechanical model may provide for real-time modelling or simulating the motion and/or deformation of the subject. Based on the determined deformation of the subject, a motion compensation may be performed and/or the planned path for the robotic instrument may be updated or adapted that may facilitate easier and/or more precise diagnostics as well as faster, easier, and more reliable procedures or interventions, for example allowing a surgeon or physician to more easily and reliably navigate the robotic instrument towards a predetermined region of interest, such as a lesion that may be achieved with reduced exposure or even without exposure of the subject to a contrast agent and/or radiation of an imaging modality as compared to traditional approaches, since the pose data of or for the robotic instrument may be acquired from existing data and/or without imposing any exposure or strain on the subject.

In an embodiment, the biomechanical model is a finite element model (FEM or FEM-model) of the subject and/or a computer graphics model that implements as-rigid-as-possible shape manipulation. The deformation of the subject due to the contact between the subject and the robotic instrument may be simulated or modelled using FEM analysis that may provide a detailed and accurate model or simulation of the deformation and may allow for a precise compensation or adaptation. The use of as-rigid-as-possible shape manipulation or deformation that certain assumption on the behavior of the subject may be made to simplify any calculations involved in executing the model, that is, in determining the deformation. This may provide for improved processing speed, for example real-time applications.

In an embodiment, the biomechanical model is generated from ultrasound data of the subject. An ultrasound measurement or ultrasound scan may be performed, and the corresponding ultrasound data or ultrasound measurements, that may describe or characterize a material or density composition of the subject, may be used to automatically, semi-automatically, or manually deduce the biomechanical model, or a part thereof, such as a stiffness sub-model of the subject or part of the subject.

The ultrasound data may be spatially and/or temporarily resolved, e.g. the respective data or dataset may be a 4D-dataset. Generating or deducing the biomechanical model from ultrasound data does not expose the subject to any potentially damaging radiation and may therefore minimize strain on the subject.

In an embodiment, the data processing unit is configured to in dependence on the pose data automatically perform a motion compensation for a combined image. The combined image is made up or generated from an image of the subject and an overlay image containing a virtual model. The combined image may be generated, for example by overlaying the overlay image on top of the image of the subject using a known 2D/3D-overlay or superimposition technique. The overlay image may, for example, include planning data, such as an instrument path for the robotic instrument, a virtual model of the subject, or of a part of the subject and/or of the robotic instrument, and/or the like. The virtual model may be a 2D-model or a 3D-model or a combination thereof. The virtual model may be predetermined, that is, created or generated prior to a respective procedure or intervention that uses or involves the robotic instrument.

The virtual model may also be generated and/or updated or adapted during the procedure or intervention, for example based on the pose data and/or live image data of the subject taken during the procedure or intervention. The image of the subject may in contrast be a medical image taken or captured by a medical imaging device or imaging modality and may therefore include or include of measured data of the subject instead of virtual or modelled data.

Combined images may improve or simplify a situational or spatial awareness or understanding for a respective surgeon or physician, and may make certain parts or features more easily visible or discernible. The pose data acquired during the procedure or intervention may then be used to update or adapted a relative positioning between the image of the subject and the overlay image to reflect a respective current spatial relation between the actual anatomy of the subject and an object that is depicted as the virtual model. Such a motion compensation is an application since it may significantly improve an accuracy and reliability in a navigation of the robotic instrument and therefore improve a success rate of corresponding procedures or interventions.

In an embodiment, the medical assistance device includes a fluoroscope for taking or capturing as the image a live fluoroscopy image of the subject while the robotic instrument is in contact with the subject. To perform the motion compensation the data processing unit is configured to continuously adjust a position of the overlay image relative to the fluoroscopy image. Basing the motion compensation on the pose data of the robotic instrument may allow for a reduced amount of contrast agent for the fluoroscopy and/or a reduced frame rate with which the live fluoroscopy image or images or video is captured or taken without at the same time compromising an accuracy of the combined image, i.e. the correct spatial relation or relative positioning of the fluoroscopy image and the overlay image that provides an improved accuracy and reliability for navigation of the robotic instrument in situations or areas of the subject where the anatomy of the subject is difficult to image, for example due to low soft tissue contrast and/or relative sparseness of contrasted vessels around the robotic instrument as might be the case for navigating the robotic instrument through a system of airways of the subject.

In an embodiment, the medical assistance device includes a data store containing as the image of the subject a pre-interventional or pre-op dataset of the subject, for example, the undisturbed image data, as the overlay image. The data store contains a segmentation of the subject derived from or based on the pre-interventional image dataset. To perform the motion compensation the data processing unit is configured to continuously adjust an outline or area of the segmentation relative to the pre-interventional image dataset. An anatomically correct and up-to-date representation of the actual anatomy of the subject may be made available even without or with reduced exposure of the subject to potentially damaging radiation, such as x-rays. For example, if the robotic instrument is moved and it is determined that its current position intersects or overlaps a volume of space that according to the pre-interventional image dataset is occupied by a part of the subject, the part of the subject may be displaced or deformed to account for the presence of the robotic instrument in the area or volume of space, since the subject and the robotic instrument cannot occupy the same volume of space at the same time.

Embodiments provide high accuracy and reliability by taking into account an actual pose and/or motion of the robot and not necessarily only assuming a predetermined shape or geometry of the robotic instrument since the robotic instrument itself may be flexible or deformable and the mechanical or physical contact between the subject and the robotic instrument may not only lead to a deformation of the subject, but also to a deformation of the robotic instrument. A relative stiffness or flexibility of the robotic instrument with respect to or in comparison with the stiffness or flexibility of the subject or vice versa may be determined and taken into account.

In an embodiment, the medical assistance device includes a data store containing as the image a pre-interventional or pre-operative dataset of the subject, for example, the undisturbed image data. To perform the motion compensation the data processing unit is configured to continuously adjust a position and/or an outline of a predetermined region of interest of the subject relative to the pre-interventional image dataset. The data store and/or the pre-interventional image dataset may be the same data store and/or pre-interventional image dataset, respectively, as mentioned above. The predetermined region of interest may, for example, be or include or contain a specific anatomical feature of the subject, such as a lesion, a calcification, a stenosis, a tumor, and/or the like.

The region of interest may be automatically determined by an image processing or object identification algorithm Additionally, or alternatively, the region of interest may be marked by a respective physician, for example in the pre-interventional image dataset and/or in a live image of the subject taken or captured during the respective procedure or intervention using the robotic instrument. Adjusting the position and/or outline of the region of interest relative to the pre-interventional image dataset may make the respective surgeon or physician aware of a motion, displacement, shift in position, or deformation of the region of interest during the intervention due to the insertion or movement and/or another effect of the robotic instrument. This may provide for a more accurate and reliable navigation of the robotic instrument to the region of interest.

The above-mentioned embodiments may be combined with each other to further improve an accuracy and/or reliability of the navigation of the robotic instrument and/or a depiction of the subject, and/or as a plausibility check.

In an embodiment, the medical assistance device, for example, the data processing unit, is configured to automatically generate a control signal for the robotic instrument. The control signal contains instructions for an automatic movement or adjustment of the robotic instrument against the subject to automatically determine a property, for example stiffness or flexibility, of the subject as a parameter or parameter value for the biomechanical model.

For example, the control signal may cause the robotic instrument to move itself or a specific part or section of itself with a specified force and/or for a specified distance. A force, pressure, and/or deformation of the robotic instrument occurring during this movement or motion of the robotic instrument may be measured using the sensor system of the robotic instrument. The measured force, pressure, and/or deformation acting upon the robotic instrument during the motion or movement specified by the control signal, and/or a force, energy and/or power required to achieve the motion or movement may depend on the properties, or characteristics of the surrounding tissue, i.e. of the subject, and may therefore be used as a basis to determine or deduce the properties or characteristics of the subject that may provide for a direct measurement of the corresponding property, or characteristic of the subject, that also may provide for modelling or simulating the motion, behavior, displacement, and/or deformation of the subject during the procedure or intervention using the robotic instrument with improved accuracy.

An amount or influence of any generalizations or assumptions about an individual or a specific subject may be limited. For example, individual sizes and/or placements of calcifications or stenosis may significantly change the stiffness and/or flexibility of one subject compared to the same part of a different subject. Using the robotic instrument to determine one or more parameters or parameter values for the biomechanical model may be advantageous, since no additional probe or sensor has to be applied to or inserted into the subject, resulting in an easier, more efficient, and less stressful procedure.

In an embodiment, a system including the medical assistance device and the robotic instrument, that is connected to the medical assistance device via a data connection or data link is provided. Providing the medical assistance device and the robotic instrument as a combined system may prevent any potential incompatibilities between the data measured or provided by the robotic instrument and data required or expected by the medical assistance device.

In an embodiment, the robotic instrument includes a positional sensor system configured to automatically determine the pose data for the robotic instrument itself. The robotic instrument is further configured to provide the pose data to the medical assistance device over the data connection. The robotic instrument may include a control unit that may include a communication unit. The robotic instrument may acquire or measure or determine, and provide the pose data, for example the pose, a motion, and a shape or geometry or configuration of the robotic instrument, by itself, meaning that no additional external tracking system is required that reduces a complexity and effort needed for using and applying the robotic instrument. The embodiment may function reliably, since, for example, issues of obfuscation or interference of or with an external tracking system may be avoided.

Additionally, the sensor system of the robotic instrument may also provide force and/or momentum data indicating a force, a momentum, and/or a pressure applied by, applied to, or acting upon the robotic instrument. The quantities may not be easily measured using an external tracking system, but may provide for an improved modelling, simulation, or estimation of the motion, displacement, or deformation of the subject. The sensor system of the robotic instrument may, for example, include one or more accelerometers, fiber Bragg gratings, IMUs (inertial measurement units), strain sensors, force sensors, pressure sensors, angulation sensors, and/or the like, for one or multiple parts, segments, actuators, motors, joints, and/or axes of the robotic instrument.

The sensor system of the robotic instrument, or a positioning or navigation system of the robotic instrument, including the sensor system or processing sensor data provided by the sensor system may also include an internal model of the robotic instrument itself to determine and keep track of the pose or pose data for the robotic instrument. For example, joint positions or angulations of joints of the robotic instrument may be automatically measured and/or determined and tracked by the sensor system or the positioning or navigation system of the robotic instrument based on the motion and/or geometry data or pose data according to the positional sensor system.

The pose data of the robotic instrument may be measured or determined by the positional sensor system of the robotic instrument according to or relative to an internal coordinate system of the robotic instrument. The internal coordinate system may be registered to the coordinate system of the medical assistance device and/or the coordinate system of the undisturbed image data or an imaging device or imaging modality used for capturing the undisturbed image data and/or live image data of the subject during the procedure or intervention. The pose data of the robotic instrument may be measured or determined relative to an initial or starting pose or reference pose of the robotic instrument. For example, the robotic instrument may be placed in the reference pose at a beginning of the procedure and may in the reference pose be imaged by the medical assistance device or an imaging device or modality connected thereto to establish the registration, that is, the spatial relation between the respective coordinate systems. Alternatively, both the coordinate systems of the robotic instrument and of the medical assistance device or imaging device or imaging modality may be registered with respect to a coordinate system that is fixed with respect to the world and/or a surrounding room in which the medical assistance device and/or the robotic instrument is placed.

For performing one or more of the mentioned registrations an automatic or semi-automatic registration between the coordinate systems may be performed using any of a number of established well-known techniques and methods to provide for a consistent processing and combination of respective data, such as sensor data acquired and provided by the sensor system of the robotic instrument and any image data of the subject.

Embodiments provide a method for determining a deformation of a subject. This method according to the present invention includes the step of acquiring undisturbed image data of the subject and pose data of a robotic instrument relative to a coordinate system of the undisturbed image data. The undisturbed image data shows the subject while not being deformed by the robotic instrument. The method further includes the step of processing the pose data to determine the deformation of the subject due to a physical contact between the robotic instrument and the subject based on a biomechanical model of the subject. The undisturbed image data and a pose and/or motion of the robotic instrument specified by the pose data is or are provided as input to the biomechanical model. The biomechanical model is predetermined, or generated and/or updated based on an absolute or relative strain and/or a stiffness—of the subject and/or the robotic instrument—measured by a sensor system of the robotic instrument, and acquired by the data acquisition unit. The objects, such as the robotic instrument, its sensor system, and the subject, mentioned in conjunction with or as part of the method may be the corresponding objects mentioned in conjunction with the medical assistance device and/or the system. In turn, the medical assistance device, and/or the system may be configured to, automatically or semi-automatically, carry out the method. Consequently, any steps, procedures, processes, or actions described in conjunction with the medical assistance device and/or the system may be part of the method according to the present invention in the form of, potentially optional, additional process steps.

In an embodiment, the biomechanical model is predetermined based on or generated from the undisturbed image data. In contrast to a generic model of the subject, such as a generic or general model of an organ, basing the biomechanical model on the actual image data of the specific subject in each case may advantageously lead to a more accurate or relevant modelling. For example, differences between subjects or patients in size or initial shape and/or a way the subject, for example an organ, is embedded into and/or connected to surrounding tissues may automatically be taken into account when basing the biomechanical model on the respective undisturbed image data.

In an embodiment, a registration between the coordinate system of the undisturbed image data and a coordinate system in which the pose data is determined, for example a coordinate system of the sensor system of the robotic instrument configured to determine the pose data, is performed, automatically or semi-automatically.

In an embodiment, live image data of the subject and of the robotic instrument is taken or captured by an imaging modality or imaging device that is configured to picture, that is, able to detect, the robotic instrument while the robotic instrument is in contact with the subject. The live image data is acquired by the data acquisition unit, and the pose data is inferred from the live image data. An image-based approach may be taken to determine the pose data, and to track the robotic instrument, a pose, a motion, and/or a geometry or shape. The approach may be useful and easy to implement as the live image data might be taken anyway so that no additional hardware or preparation is required and the robotic instrument may relatively easily be built and/or the imaging device or imaging modality be adapted or tuned so that the robotic instrument may reliably be detected in the live image data. For example, the robotic instrument may contain metal parts or markers, that are more easily and reliably detectable and discernible than, for example, a soft tissue of the subject under x-ray imaging. The robotic instrument may then be reliably identified and tracked through the live image data independently of in which part of the patient or subject the robotic instrument is located or navigated. The image-based tracking of the robotic instrument may be combined with any and/or all of the other possibilities for acquiring or determining the pose data described that may result in an overall improved accuracy and/or reliability of the determination of the deformation of the subject.

An embodiment provides a computer program or computer program product including instructions that, when the computer program is executed by a computer, for example by the medical assistance device and/or the system, cause the computer to carry out the steps of the method. The method may take the form of the computer program or a program code, including instructions that, when carried out by the medical assistance device or by the system cause the instructions to perform or carry out the method. The steps of the method may be interpreted or implemented as functional parts or blocks of the computer program.

Embodiments provide a computer-readable storage medium that stores the computer program.

To automatically or semi-automatically carry out the method, the medical assistance device and/or the system may each contain or include a computer-readable storage medium as well as a processor connected thereto, such as a microprocessor, a microchip, or a microcontroller, to execute the computer program or program code stored on the respective computer-readable storage medium.

Embodiments may be used, applied, or executed during or in parallel to an interventional procedure.

The embodiments described for at least one aspect, that is, at least for the medical assistance device, the system, the method, the computer program, and the computer-readable storage medium, as well as the corresponding advantages may be applied to any and/or all aspects.

BRIEF DESCRIPTION OF THE FIGURES

FIG. 1 depicts a schematic drawing of a system including a medical imaging and assistance device and a robotic instrument according to an embodiment.

FIG. 2 depicts an example of a schematic flow chart for a method for determining and processing a deformation of a subject during a procedure involving a robotic instrument according to an embodiment.

DETAILED DESCRIPTION

FIG. 1 schematically depicts a drawing of a system including a medical assistance device 1 and a flexible or deformable robotic instrument 2. The medical assistance device 1 includes an imaging system or imaging device, that includes of a C-arm on which a radiation source 3 and a corresponding opposing detector 4 are mounted. For example, the imaging device or the medical assistance device 1 may be a CT-device. The medical assistance device 1 or its imaging device may, however, also be or include another imaging modality, such as for example for magnetic resonance imaging device and/or ultrasound imaging device.

On a patient table located between the radiation source 3 and the detector 4, there is arranged a patient 5 as a subject to be imaged. For example, a lung 6 of the patient 5 is to be examined and/or treated as the subject using the medical assistance device 1 and the robotic instrument 2. The medical assistance device 1 also includes a data processing device 7, that is equipped and configured to acquire image data of the patient 5, for example of the lung 6, taken or captured by the detector 4, and to process the image data. The data processing device includes a data acquisition unit and a data processing unit and also includes a storage medium 8 and connected thereto a processor 9. Stored on the storage medium 8 is a computer program that includes instructions for the data processing device 7 or for the medical assistance device 1. The computer program may be or include a control program and/or an operating system for the medical assistance device 1 or the system including the medical assistance device 1 and the robotic instrument 2.

The robotic instrument 2 may be connected to the medical assistance device 1, and for example, to the data processing device 7, via a wireless data link over which sensor data measured by a sensor system of the robotic instrument 2 may be acquired by the data processing device 7, and instructions or control signals may be transmitted from the data processing device 7 to the robotic instrument 2. The robotic instrument 2 may for example include or be held and guided by a light industrial multi-axis robot, for example a 6-axis robot, and be or be equipped with an endoscope, a bronchoscope, a biopsy needle, and/or the like.

Images, image data, and/or visualizations generated or adapted by the data processing device 7 may be displayed by a display device 10 connected to the data processing device 7. The display device 10 may be part of the medical assistance device 1 or located separately or remotely.

The computer program stored on the storage medium 8 or its functions, parts, or blocks are depicted as a flow chart 11, an example of which is depicted shown in FIG. 2. In a step S1 a pre-operative image or a dataset of the lung 6 is taken that may be or include a 3D-CT- or MR-image and/or a cone-beam CT-image (CBCT), that may be taken or captured by the medical assistance device 1. The pre-operative image dataset is taken before the robotic instrument 2 is applied to or inserted into the patient 5 and therefore represents undisturbed image data of the patient 5 or the lung 6, respectively, showing it in an undisturbed, uninfluenced, or undeformed state.

In a process step S2 the pre-operative or pre-interventional image dataset is segmented. The lung 6 and/or parts thereof, such as specific airways, may be defined or distinguished from the surrounding tissue or image data. A model of the lung 6 or parts thereof may be generated from the pre-operational or pre-interventional image dataset.

In a process step S3 a biomechanical model of the lung 6, including surrounding tissues, is generated that may be based on the model of the lung 6 generated as or from the segmentation of the pre-operative or preoperational image dataset.

Parallel to carrying out the method described following the flow chart 11, the examination or treatment procedure of the patient 5 may be performed by medical personnel, such as a surgeon or physician. The robotic instrument 2 is applied to or inserted into the lung 6.

In a process step S4 a fluoroscopic live image of or live video the long 5 and the robotic instrument 2 is then taken by the medical assistance device 1, for example the radiation source 3 and the detector 4.

If the preoperational image dataset has not been taken with the medical assistance device 1, and/or the patient 5 has been moved since the pre-operative image dataset has been taken, a registration between the pre-operative image dataset and the fluoroscopic live image may be performed in a process step S5. An internal coordinate system of the robotic instrument 2, specifically of the internal sensor system of the robotic instrument 2, and the medical assistance device 1 and, if applicable, the pre-operative image data set is performed.

In a process step S6 the data processing device 7 generates a control signal and transmits the control signal to the robotic instrument 2. The control signal causes the robotic instrument 2 to move in a certain way and/or with a certain force and/or a certain distance specified by the control signal, and to measure a resulting or required force and/or pressure and/or deformation of the robotic instrument 2 and/or the lung 6. Corresponding measured sensor data is then transmitted from the robotic instrument 2 back to the data processing device 7, that, based thereon, determines at least one property or characteristic, such as a stiffness, a flexibility, and/or a shape, of the lung 6 or a part thereof as a parameter or parameter value for the biomechanical model.

In a process step S7, the biomechanical model is then updated accordingly. Alternatively, the biomechanical model may also be generated, for example, if the biomechanical model was not been provided in the process step S3.

Based on the pose data acquired by the data processing device 7 from the robotic instrument 2, and on the available image data of the lung 6 the motion and/or deformation of the lung 6 is in a process step S8 continuously determined, that is, modelled or simulated using the biomechanical model, while the robotic instrument 2 is navigated inside the lung 6 to a predetermined region of interest.

In a process step S9 the data processing device 7 automatically performs a motion compensation based on the determined deformation of the lung 6. The data processing device 7 may, for example, update a position of an overlay image relative to image data, such as the fluoroscopy images, during the ongoing procedure or intervention to provide the respective physician with an accurate depiction of a current anatomical situation.

Multiple indicated program loops 12 in the flow chart 11 indicate that one or more of the described process steps may be repeated or looped during operation of the medical assistance device 1 or of the system comprising the medical assistance device 1 and the robotic instrument 2.

The method described uses a robotic system that steers the robotic instrument 2, for example, a flexible catheter or endoscopic instrument. The robotic instrument 2 or at least a part thereof shall be visible in x-ray images taken by the medical assistance device 1 so that the robotic instrument 2 may be recognized or detected in the x-ray images. The robotic instrument 2 is able to give or describe its global absolute position or pose with respect to a predetermined coordinate system. A registration is performed between the coordinate system of the robotic instrument 2 and a coordinate system of a respective imaging system used to take or capture images of the respective subject and the robotic instrument 2, i.e. the x-ray images. An image-based registration may be performed.

Other registration methods may be used. For example, the registration between the coordinate systems of the robotic instrument 2 and the imaging system, for example the medical assistance device 1, used to take the pre-of image dataset and/or intra-operative images, such as the mentioned fluoroscopy images, may be done using a tracking system, for example an electromagnetic tracking system. A segmentation of an intra-body structure, such as the lung 5, is performed where the robotic instrument 2 is inserted into the subject, i.e. the patient 5. For example, one or more airways of the patient 5 or the lung 6 may be segmented by or such a segmentation may be provided to the data processing device 7. The segmentation may be achieved using the pre-op image dataset, such as a previously acquired CT- or MR-3D-image and/or an intra-op cone-beam CT-image acquired without the presence of the robotic instrument 2 in the patient 5 or in the lung 6. The biomechanical model of the segmented airways and/or of lesions and/or of organ or vessel deformation is also generated or provided by or to the data processing device 7. The biomechanical model may use FEM analysis, a computer graphics model, a stiffness model deduced from a 4D-dataset, a stiffness model deduced from ultrasound data of the patient 5 or the lung 6, and/or the like.

To determine the respective current anatomical deformation status of the lung 6, the deformation may be calculated during the insertion or navigation of the robotic instrument 2 by relating the absolute position of the robotic instrument 2 with the available anatomical segmentation, that may be performed on to pre-op data or intra-up data, such as a cone-beam CT-image, and with the biomechanical model of lesion-, airway-, and/or organ-deformation. The absolute position of the robotic instrument 2 may be delivered or provided by the robotic instrument 2 itself and corresponding position data or pose data may then be used by the data processing device 7 to infer a current anatomical deformation field or a motion field for the lung 6, e.g. for a respective subject. The term "deformation field" or "motion field" refers to a movement, motion, and/or deformation of parts or volume elements of the subject during operation of the robotic instrument. The motion and/or deformation of the subject or parts thereof as the deformation field or motion field may be provided as spatially and/or time-resolved data. The motion and/or deformation of the subject may, be or include a translatory and/or a rotational part and/or a deformation part, e.g. a movement or motion of parts of the subject relative to other parts of the subject. The deformation field or motion field may, for example, be used to provide an update of an overlay image onto a respective current fluoroscopy image and/or to generate and show an updated segmentation and/or lesion position on the pre-operative dataset.

In addition to determining the current anatomical deformation status another goal may be to generate or update parameters or parameter values of the biomechanical model. The robotic instrument 2 may measure a stiffness or strain of the respective subject, for example of the airways of the patient 5 or of the lung 6, by using strain and stiffness sensors that may be done continuously or regularly during use or navigation of the robotic instrument 2 in or during the intra-body procedure. By actively inducing specific forces and/or strain it is possible to estimate anatomical deformation and stiffness of the airways or the lung 6 to estimate or update the corresponding parameters or parameter values of the biomechanical model for one or more respective anatomical parts or regions of the respective subject, and/or to establish a biomechanical model of the respective subject during the procedure.

The described examples show how a robotic-based anatomical deformation estimation may be realized to provide technical assistance to medical personnel during a procedure involving a robotic tool, such as the robotic instrument 2.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical assistance device, the medical assistance device comprising:
   a fluoroscope configured to capture an image comprising a live fluoroscopy image of a subject while a robotic instrument is in contact with the subject;
   a data acquisition unit configured to acquire undisturbed image data of the subject comprising a patient or a part of the patient and pose data of the robotic instrument relative to a coordinate system of the undisturbed image data, wherein the undisturbed image data shows the subject while not being deformed by the robotic instrument; and
   a data processing unit connected to the data acquisition unit and configured to determine a deformation of the subject due to a physical contact between the robotic instrument and the subject based on a biomechanical model of the subject and based on the undisturbed image data and a pose, motion, or pose and motion of the robotic instrument specified by the pose data provided as input to the biomechanical model, the data processing unit further configured to perform motion compensation for a combined image generated from the live fluoroscopy image of the subject and an overlay image containing a virtual model based on the pose data, wherein the data processing unit is configured to continuously adjust a position of the overlay image relative to the live fluoroscopy image;
   wherein the biomechanical model is at least one of predetermined, generated, or updated based on a strain, a stiffness, or the strain and the stiffness measured by a sensor system of the robotic instrument and acquired therefrom by the data acquisition unit.

2. The medical assistance device of claim 1, wherein the biomechanical model is a finite element model of the subject and a computer graphics model that implements as-rigid-as-possible shape manipulation.

3. The medical assistance device of claim 1, wherein the biomechanical model is generated from ultrasound data of the subject.

4. The medical assistance device of claim 1, further comprising:
   a data store configured to contain as the image a pre-interventional image dataset of the subject and a segmentation of the subject used as the overlay image based on the pre-interventional image dataset;
   wherein to perform the motion compensation the data processing unit is configured to continuously adjust an outline or area of the segmentation relative to the pre-interventional image dataset.

5. The medical assistance device of claim 4, wherein the pre-intervention image is the undisturbed image data.

6. The medical assistance device of claim 1, further comprising:
   a data store configured to contain as the image a pre-interventional image dataset of the subject;
   wherein to perform the motion compensation the data processing unit is configured to continuously adjust a position, an outline, or a position and an outline of a predetermined region of interest of the subject relative to the pre-interventional image dataset.

7. The medical assistance device of claim 1, wherein the data processing unit is further configured to automatically generate a control signal for the robotic instrument containing instructions for an automatic movement of the robotic instrument against the subject to automatically determine a property of the subject as a parameter for the biomechanical model.

8. The medical assistance device of claim 7, wherein the property is a stiffness or flexibility of the subject.

9. A system comprising:
   a robotic instrument comprising a positional sensor system configured to automatically determine a pose data and to provide the pose data to a medical assistance device over a data connection; and the medical assistance device comprising:
a fluoroscope configured to capture as an image a live fluoroscopy image of a subject while the robotic instrument is in contact with the subject;
a data acquisition unit configured to acquire undisturbed image data of the subject comprising a patient or a part of the patient and pose data of the robotic instrument relative to a coordinate system of the undisturbed image data, wherein the undisturbed image data shows the subject while not being deformed by the robotic instrument; and
a data processing unit connected to the data acquisition unit and configured to determine a deformation of the subject due to a physical contact between the robotic instrument and the subject based on a biomechanical model of the subject and based on the undisturbed image data and a pose, a motion, or the pose and the motion of the robotic instrument specified by the pose data provided as input to the biomechanical model, the data processing unit further configured to perform motion compensation based on the pose data by continuously adjusting a position of an overlay image containing a virtual model relative to the live fluoroscopy image;
wherein the biomechanical model is at least one of predetermined, generated, or updated based on a strain, a stiffness, or the strain and the stiffness measured by a sensor system of the robotic instrument and acquired therefrom by the data acquisition unit.

10. The system of claim 9, wherein the biomechanical model is a finite element model of the subject and a computer graphics model that implements as-rigid-as-possible shape manipulation.

11. The system of claim 9, wherein the biomechanical model is generated from ultrasound data of the subject.

12. The system of claim 9, further comprising:
a data store configured to contain as the image a pre-interventional image dataset of the subject and a segmentation of the subject used as the overlay image based on the pre-interventional image dataset;
wherein to perform the motion compensation the data processing unit is configured to continuously adjust an outline or area of the segmentation relative to the pre-interventional image dataset.

13. A method for determining a deformation of a subject comprising a patient or a part of the patient, the method comprising:
acquiring undisturbed image data of the subject and pose data of a robotic instrument relative to a coordinate system of the undisturbed image data, wherein the undisturbed image data shows the subject while not being deformed by the robotic instrument;
capturing, while the robotic instrument is in contact with the subject, live image data of the subject and of the robotic instrument by an imaging modality, wherein the live image data is acquired by a data acquisition unit and the pose data is inferred from the live image data;
processing the pose data to determine the deformation of the subject due to a physical contact between the robotic instrument and the subject based on a biomechanical model of the subject; and
performing motion compensation based on the pose data by continuously adjusting a position of an overlay image containing a virtual model relative to the live image data;
wherein the undisturbed image data and a pose, a motion, or the pose and the motion of the robotic instrument specified by the pose data is provided as input to the biomechanical model;
wherein the biomechanical model is at least one of predetermined, generated, or updated based on a strain, a stiffness, or the strain and the stiffness measured by a sensor system of the robotic instrument and acquired by the data acquisition unit.

14. The method of claim 13, wherein the biomechanical model is predetermined based on the undisturbed image data.

15. The method of claim 13, further comprising:
performing a registration between the coordinate system of the undisturbed image data and a coordinate system in which the pose data is determined.

* * * * *